United States Patent
Lei et al.

(10) Patent No.: US 10,927,089 B2
(45) Date of Patent: Feb. 23, 2021

(54) DIARYL THIOETHER PIPERAZINE COMPOUNDS, PREPARATION METHODS AND USES THEREOF

(71) Applicant: SUNSHINE LAKE PHARMA CO., LTD., Guangdong (CN)

(72) Inventors: Xin Lei, Dongguan (CN); Dongming Li, Dongguan (CN); Zhonghua Luo, Dongguan (CN); Bifei He, Dongguan (CN); Qian Wang, Dongguan (CN)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 75 days.

(21) Appl. No.: 16/308,462

(22) PCT Filed: Jun. 15, 2017

(86) PCT No.: PCT/CN2017/088493
§ 371 (c)(1),
(2) Date: Dec. 8, 2018

(87) PCT Pub. No.: WO2017/215636
PCT Pub. Date: Dec. 21, 2017

(65) Prior Publication Data
US 2019/0256482 A1 Aug. 22, 2019

(30) Foreign Application Priority Data
Jun. 16, 2016 (CN) .......................... 2016 1 0446737

(51) Int. Cl.
| | | |
|---|---|---|
| *C07D 295/192* | (2006.01) |
| *C07D 295/185* | (2006.01) |
| *C07D 405/12* | (2006.01) |
| *A61P 25/28* | (2006.01) |
| *A61P 25/24* | (2006.01) |
| *C07D 295/096* | (2006.01) |
| *A61K 31/495* | (2006.01) |
| *A61K 45/06* | (2006.01) |

(52) U.S. Cl.
CPC ........ *C07D 295/192* (2013.01); *A61K 31/495* (2013.01); *A61P 25/24* (2018.01); *A61P 25/28* (2018.01); *C07D 295/096* (2013.01); *C07D 295/185* (2013.01); *C07D 405/12* (2013.01); *A61K 45/06* (2013.01)

(58) Field of Classification Search
None
See application file for complete search history.

(56) References Cited

U.S. PATENT DOCUMENTS

| | | |
|---|---|---|
| 8,664,225 B2 | 3/2014 | Moore et al. |
| 8,722,684 B2 | 5/2014 | Bang-Andersen et al. |
| 9,101,626 B2 | 8/2015 | Faldt et al. |
| 9,125,908 B2 | 9/2015 | Bang-Andersen et al. |
| 9,550,743 B2 | 1/2017 | Giannotti et al. |
| 2005/0171061 A1 | 8/2005 | Smith et al. |
| 2016/0145224 A1 | 5/2016 | Giannotti et al. |
| 2017/0088530 A1 | 3/2017 | Tang et al. |

FOREIGN PATENT DOCUMENTS

| | | | |
|---|---|---|---|
| CN | 104829558 A | 8/2015 | |
| CN | 105461656 A | 4/2016 | |
| EP | 3023417 B1 | 6/2017 | |
| WO | 2013088255 A1 | 6/2013 | |
| WO | 2016004908 A1 | 1/2016 | |
| WO | WO2016004908 | * 1/2016 | |
| WO | WO-2016004908 A1 | * 1/2016 | ............. A61P 25/24 |
| WO | 2016079751 A2 | 5/2016 | |
| WO | WO-2017125504 A1 | * 7/2017 | ......... C07D 295/096 |
| WO | 2017162536 A1 | 9/2017 | |

OTHER PUBLICATIONS

Berge et al., Pharmaceutical Salts. Journal of Pharmaeutical Sciences, 1977, 66, 1-19.*
Chemical Abstract Registry No. 1928726-88-8, indexed in the Registry File on STN CAS Online Jun. 9, 2016.*
Translation of the abstract of CN104829558.
Translation of the abstract of CN101472906.
ISR of PCT/CN2017/088493, mailed on Aug. 30, 2017. (Eng. Translation only).
Written Opinion of the ISA of PCT/CN2017/088493, dated Aug. 30, 2017. (Eng. translation only).
Translation of CN105461656.
Translation of CN104829558.
Translation of ISR of PCT/CN2017/088493, mailed on Aug. 30, 2017.
Translation of Written Opinion of the ISA of PCT/CN2017/088493, dated Aug. 30, 2017.

* cited by examiner

*Primary Examiner* — Po-Chih Chen
(74) *Attorney, Agent, or Firm* — Kam Wah Law

(57) ABSTRACT

The invention relates to a diaryl thioether piperazine compound, a preparation method and use thereof. Specifically, the compound is a compound of Formula (I), wherein HX is $C_{10-20}$ fatty acid or pamoic acid.

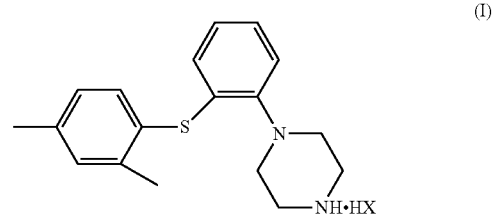

(I)

11 Claims, 1 Drawing Sheet

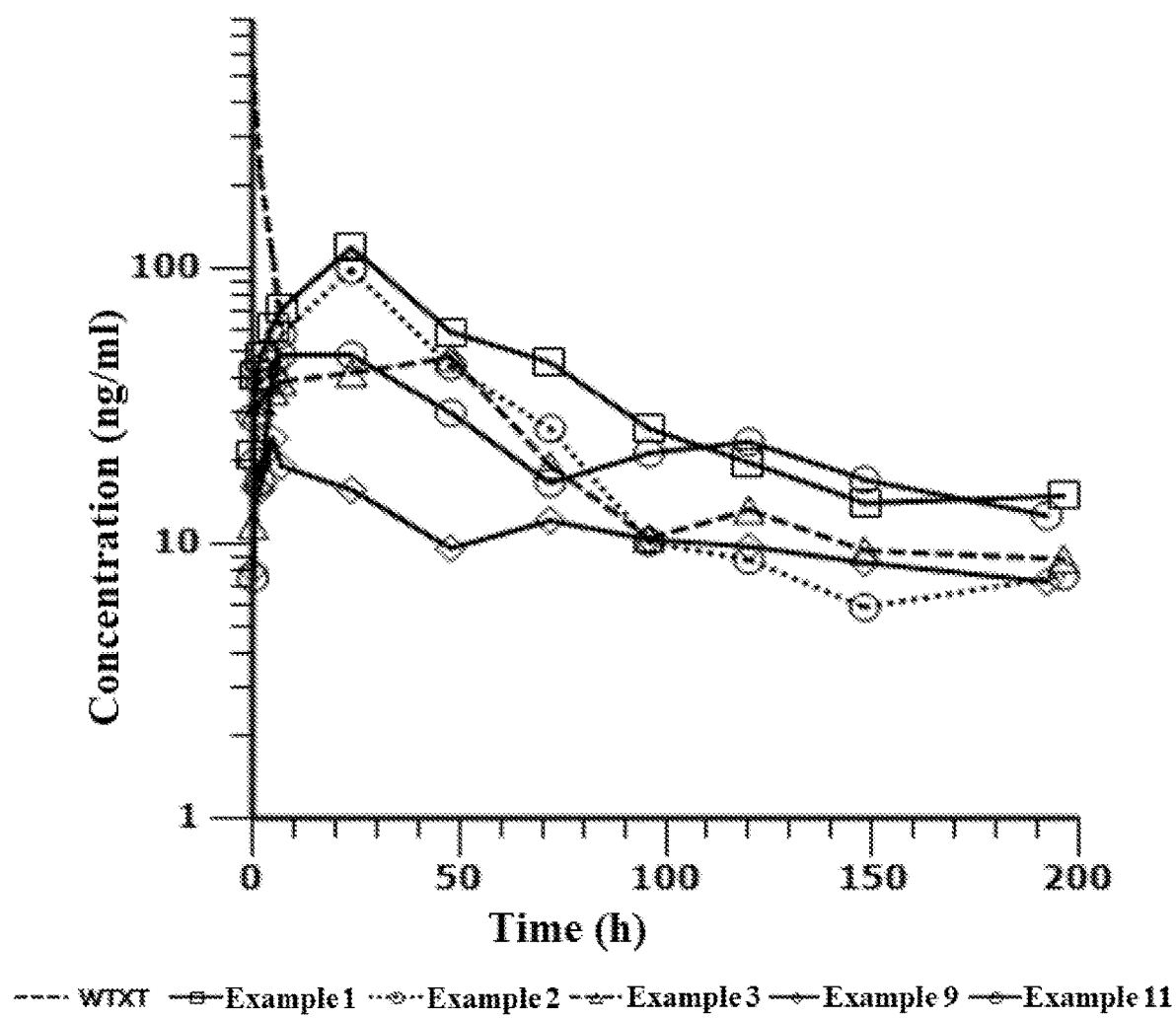

DIARYL THIOETHER PIPERAZINE COMPOUNDS, PREPARATION METHODS AND USES THEREOF

CROSS REFERENCE TO RELATED APPLICATIONS

This is a U.S. national stage application of the International Patent Application No. PCT/CN2017/088493, filed Jun. 15, 2017, which claims priority to Chinese Patent Application No. 201610446737.5, filed Jun. 16, 2016, both of which are incorporated herein by reference in their entirety.

FIELD OF THE INVENTION

The invention relates to the field of medicine, and in particular, the invention relates to compounds, preparation methods and applications thereof, and more particularly, the invention relates to compounds represented by Formula (I) and Formula (II), preparation methods thereof, pharmaceutical compositions and applications thereof.

BACKGROUND OF THE INVENTION

Major depressive disorder (MDD) is a common mental disease, mainly characterized by low mood, reduced interest, pessimism, slow thinking, lack of initiative, self-blame, poor diet, poor sleep, worry about suffering from various diseases, feeling a lot of discomfort in the body, and a patient with serious major depressive disorder may have suicidal thoughts and behaviors.

Vortioxetine hydrobromide (Lu AA21004, Vortioxetine Hydrobromide) is a new class of chemical antidepressant developed by Lundbeck and Japan's Takeda Pharmaceutical Co., Ltd., and was approved by the Food and Drug Administration (FDA) on Sep. 30, 2013, for the treatment of major depressive disorder in adults. The package inserts of vortioxine indicates that the drug needs to be taken once a day.

However, the current drug vortioxetine for the treatment of major depressive disorder remains to be improved.

SUMMARY OF THE INVENTION

The present invention aims to solve at least one of the technical problems to some extent in the related art.

A batch of diaryl thioether piperazine compounds have been prepared by using 1-(2-((2,4-dimethylphenyl)thio)phenyl)piperazine as a raw material in the invention, and it has been unexpected discovered that these compounds have good sustained release effects in animals by pharmacological experiments, and the sustained release effect of one dose can be maintained for one week to several weeks. If it can be used in clinic, it is possible to greatly reduce the frequency of taking this medicine and make the patient more conveniently take this medicine.

In one aspect, provided herein is a compound of Formula (I),

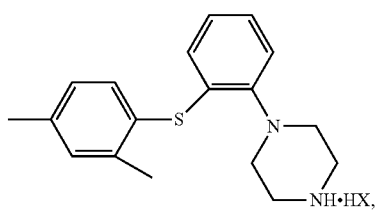
(I)

wherein, HX is $C_{10-20}$ fatty acid or pamoic acid. The compound of Formula (I) can be used for the treatment of major depressive disorder, and has good pharmacokinetic properties and low solubility, so that the compound of Formula (I) can be slowly released and exerts efficacy in the body. That is to say, the compound of Formula (I) can be pharmacologically effective for a relatively long period in the body, thereby reducing the times of administration and making the administration more convenient.

According to some embodiments of the invention, HX is stearic acid, palmitic acid, lauric acid or pamoic acid.

According to some embodiments of the invention, the compound has at least one of the following structures,

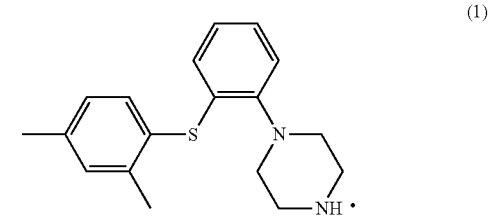
(1)

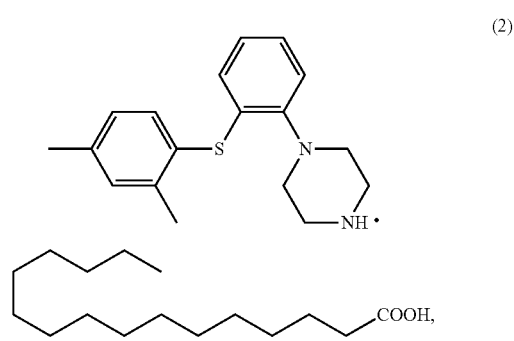
(2)

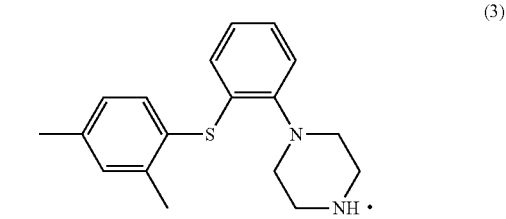
(3)

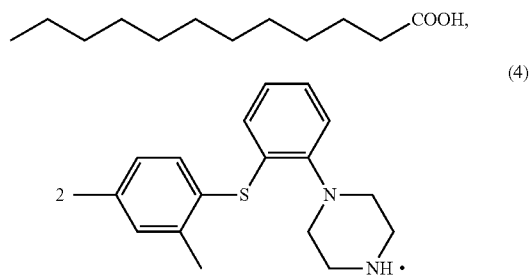
(4)

-continued

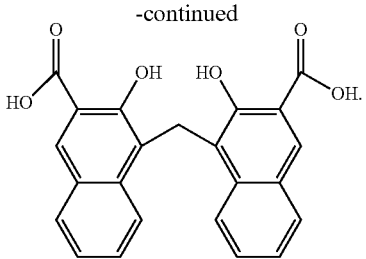

In another aspect, provided herein is a compound of Formula (II) or a stereoisomer, a tautomer, a solvate or a pharmaceutically acceptable salt thereof,

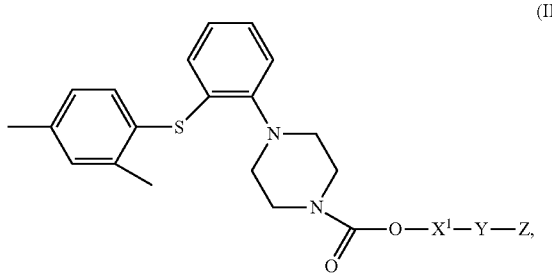

(II)

wherein,
$X^1$ is a bond or $—(CH_2)_n—$;
Y is a bond or

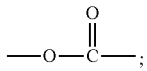

;

when Y is a bond, Z is $C_{2-10}$ alkyl, $C_{5-10}$ heteroaryl, $C_{5-10}$ heterocyclyl, wherein optionally each of the $C_{2-10}$ alkyl, $C_{5-10}$ heteroaryl and $C_{5-10}$ heterocyclyl is independently substituted with one or more R;
when Y is

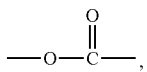

,

Z is $C_{1-20}$ alkyl, $C_{6-10}$ aryl, $C_{5-10}$ heteroaryl, $C_{5-10}$ heterocyclyl, wherein optionally each of the $C_{1-20}$ alkyl, $C_{6-10}$ aryl, $C_{5-10}$ heteroaryl and $C_{5-10}$ heterocyclyl is independently substituted with one or more R;

n is 1, 2, 3, 4 or 5;
each R is independently F, Cl, Br, I, amino, hydroxy or $C_{1-6}$ alkyl;
with the proviso that when $X_1$ is a bond and Y is a bond, Z is not tert-butyl. The compound of Formula (II) can be used for the treatment of major depressive disorder, and has good pharmacokinetic properties and low solubility, so that the compound of Formula (II) can be slowly released and exerts efficacy in the body. That is to say, the compound of Formula (II) can be pharmacologically effective for a relatively long period in the body, thereby reducing the times of administration and making the administration more convenient.

According to some embodiments of the invention, when Y is a bond, Z is $C_{2-10}$ alkyl, $C_{5-10}$ heteroaryl, $C_{5-10}$ heterocyclyl, and Z is not tert-butyl, wherein optionally each of the $C_{2-10}$ alkyl, $C_{5-10}$ heteroaryl and $C_{5-10}$ heterocyclyl is independently substituted with one or more R.

According to some embodiments of the invention, when Y is a bond, Z is ethyl, n-propyl, isopropyl, n-butyl, isobutyl, sec-butyl, n-pentyl, 2-pentyl, 3-pentyl, $C_{5-8}$ heteroaryl, $C_{5-8}$ heterocyclyl, wherein optionally each of the ethyl, n-propyl, isopropyl, n-butyl, isobutyl, sec-butyl, n-pentyl, 2-pentyl, 3-pentyl, $C_{5-8}$ heteroaryl and $C_{5-8}$ heterocyclyl is independently substituted with one or more R groups; n is 0, 1, 2 or 3; each R is independently F, Cl, Br, I, amino, hydroxy or $C_{1-3}$ alkyl.

According to some embodiments of the invention, when Y is a bond, Z is $C_{2-5}$ linear alkyl, $C_{5-7}$ heteroaryl, $C_{5-7}$ heterocyclyl, wherein optionally each of the $C_{2-5}$ linear alkyl, $C_{5-7}$ heteroaryl and $C_{5-7}$ heterocyclyl is independently substituted with one or more R; n is 1, 2 or 3; each R is independently F, Cl, Br, I, amino, hydroxy or $C_{1-3}$ alkyl.

According to some embodiments of the invention, when Y is

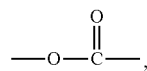

,

Z is $C_{1-20}$ alkyl, phenyl, $C_{6-8}$ aryl, $C_{5-8}$ heteroaryl, $C_{5-8}$ heterocyclyl, wherein optionally each of the $C_{1-20}$ alkyl, phenyl, $C_{6-8}$ aryl, $C_{5-8}$ heteroaryl and $C_{5-8}$ heterocyclyl is independently substituted with one or more R; n is 0, 1, 2 or 3; each R is independently F, Cl, Br, I, amino, hydroxy or $C_{1-3}$ alkyl.

According to some embodiments of the invention, the compound disclosed herein has one of the following structures, or a stereoisomer, a tautomer, a solvate, or a pharmaceutically acceptable salt thereof,

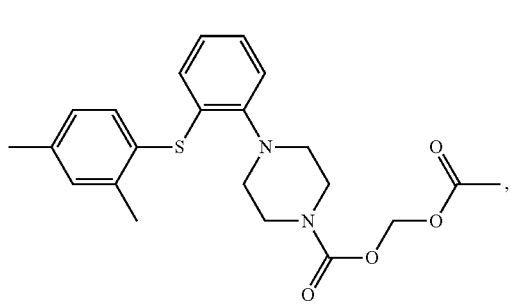

(5)

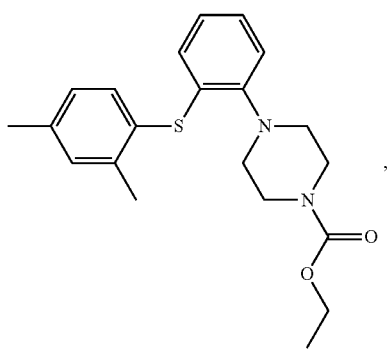

(6)

-continued
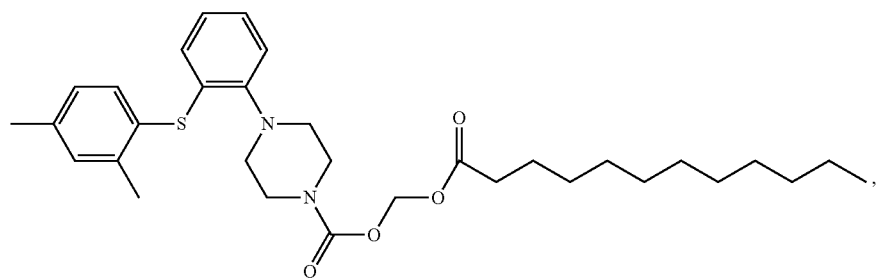
(7)
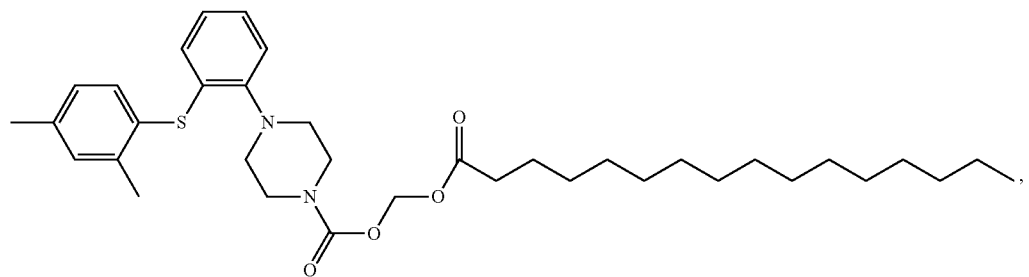
(8)
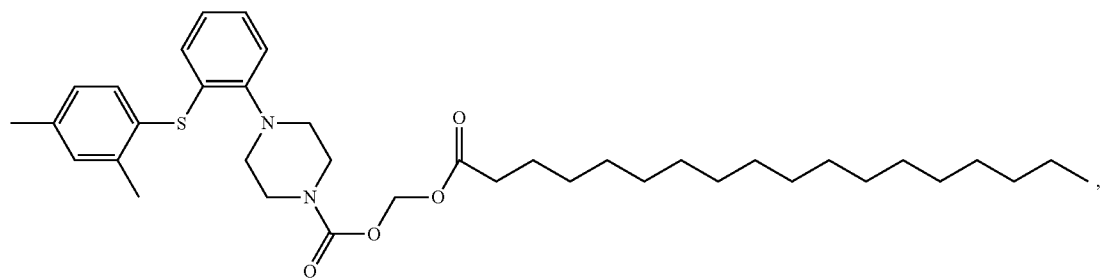
(9)
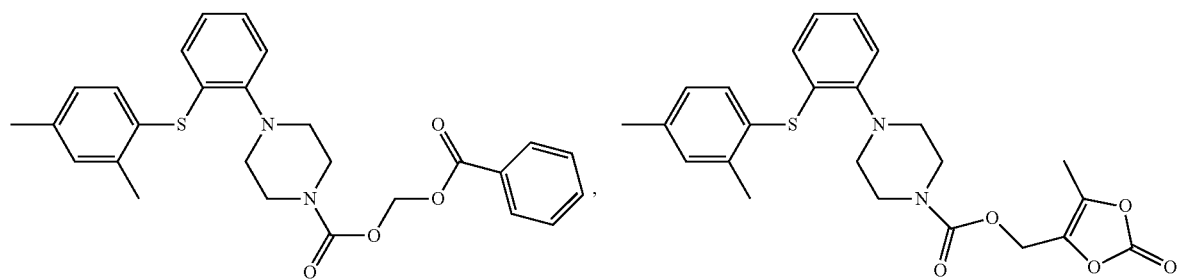
(10) (11)
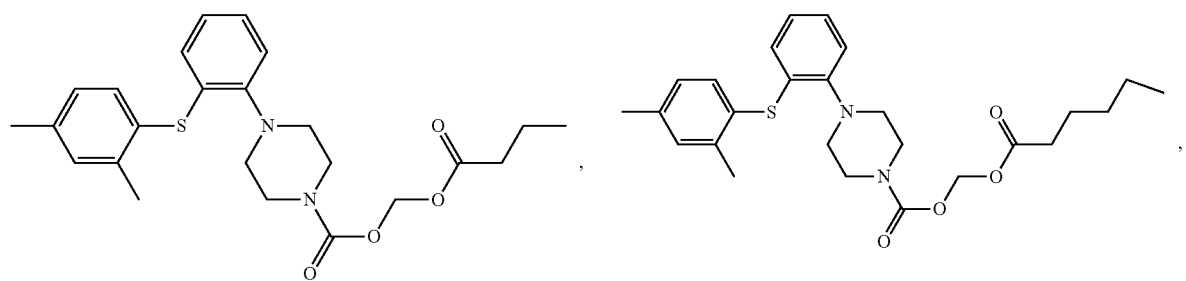
(12) (13)

-continued

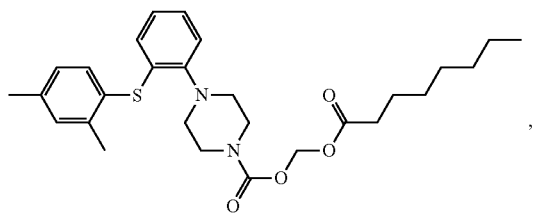
(14)

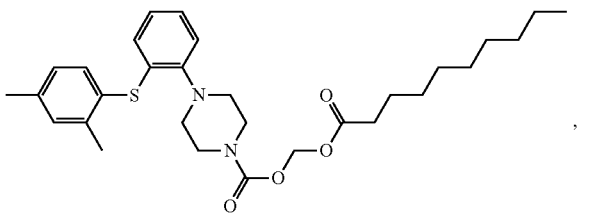
(15)

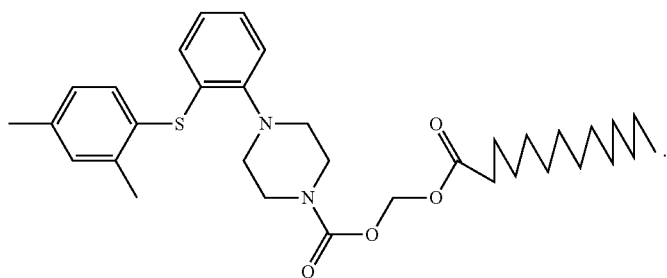
(16)

In another aspect, provided herein is a method for preparing the compound disclosed herein, which comprises (1) contacting a compound of Formula (a) with a compound of Formula (b) to obtain a compound of Formula (c);

(2) contacting the compound of Formula (c) with a compound of Formula (d) to obtain a compound of Formula (III), wherein, $X^1$ is a bond or —$(CH_2)_n$—;

each $R^1$ is independently F, Cl, Br or I;

Z is $C_{1-20}$ alkyl, $C_{6-10}$ aryl, $C_{5-10}$ heteroaryl, $C_{5-10}$ heterocyclyl, wherein optionally each of the $C_{1-20}$ alkyl, $C_{6-10}$ aryl, $C_{5-10}$ heteroaryl and $C_{5-10}$ heterocyclyl is independently substituted with one or more R;

n is 1, 2, 3, 4 or 5;

each R is independently F, Cl, Br, I, amino, hydroxy or $C_{1-6}$ alkyl,

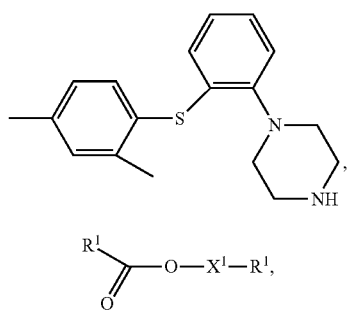
(a)

(b)

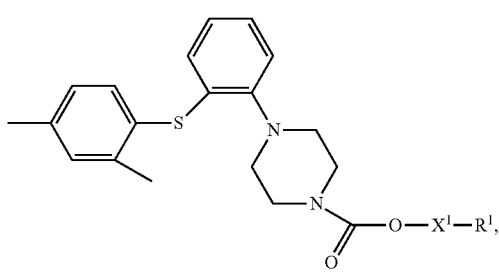
(c)

Z—COOH, (d)

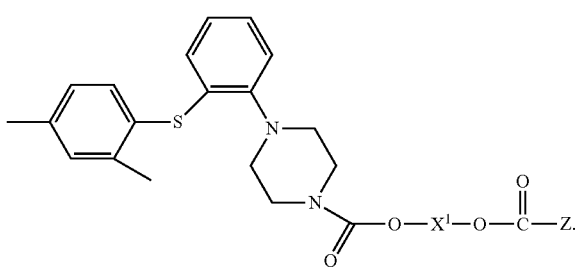
(III)

According to some embodiments of the invention, Z is $C_{1-20}$ alkyl, phenyl, $C_{6-8}$ aryl, $C_{5-8}$ heteroaryl, $C_{5-8}$ heterocyclyl, wherein optionally each of the $C_{1-20}$ alkyl, phenyl, $C_{6-8}$ aryl, $C_{5-8}$ heteroaryl and $C_{5-8}$ heterocyclyl is independently substituted with one or more R; n is 0, 1, 2 or 3; each R is independently F, Cl, Br, I, amino, hydroxy or $C_{1-3}$ alkyl.

In another aspect, provided herein is a pharmaceutical composition comprising the compound of Formula (I), (II), or the compound of Formula (III) prepared by the method described above.

According to some embodiments of the invention, the pharmaceutical composition further comprises at least one of a pharmaceutically acceptable carrier, excipient, diluent, adjuvant or vehicle.

According to some embodiments of the invention, the pharmaceutical composition further comprises an additional therapeutic agent, wherein the additional therapeutic agent is used for treating depressive disorder.

In another aspect, provided herein is use of the compound of Formula (I), the compound of Formula (II), the compound of Formula (III) prepared by the method described above, or the pharmaceutical composition described above in the manufacture of a medicament, wherein the medicament is used for treating a depressive disorder in a patient.

In another aspect, provided herein is the compound of Formula (I), the compound of Formula (II), the compound of Formula (III) prepared by the method described above, or the pharmaceutical composition described above for use in treating a depressive disorder in a patent.

In another aspect, provided herein is a method of treating a depressive disorder in a patent. According to some embodiments of the invention, the method comprises administering to the patient the compound of Formula (I), the compound of Formula (II), the compound of Formula (III) prepared by the method described above, or the pharmaceutical composition described above.

According to some embodiments of the invention, the method further comprises administering to the patient an additional therapeutic agent, wherein the additional therapeutic agent is used for treating depressive disorder.

DEFINITIONS AND GENERAL TERMINOLOGY

The term "optional" or "optionally" refers to that a subsequently described event or circumstance may but need not occur, and that the description includes instances that the event or circumstance occurs and instances that the event or circumstance does not occur.

In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

The term "comprise" is an open expression, it means comprising the contents disclosed herein, but don't exclude other contents.

At various places in the present specification, substituents of compounds disclosed herein are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

The term "alkyl" or "alkyl group" refers to a saturated linear or branched-chain monovalent hydrocarbon radical of 1 to 20 carbon atoms. Unless otherwise specified, the alkyl group contains 1 to 20 carbon atoms. In some embodiments, the alkyl group contains 1-10 carbon atoms. In other embodiments, the alkyl group contains 1-8 carbon atoms. In other embodiments, the alkyl group contains 1-6 carbon atoms. In still other embodiments, the alkyl group contains 1-4 carbon atoms, and in yet other embodiments, the alkyl group contains 1-3 carbon atoms. The alkyl group is optionally substituted with one or more substituents disclosed herein.

Some non-limiting examples of the alkyl group include, but are not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), n-heptyl, n-octyl, and the like.

The term "heteroatom" refers to one or more of oxygen (O), sulfur (S), nitrogen (N), phosphorus (P) or silicon (Si), including any oxidized form of nitrogen (N), sulfur (S), or phosphorus (P); primary amine, secondary amine, tertiary amine and quaternary ammonium salts; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "heterocyclic", "heterocyclyl", or "heterocyclic ring" as used interchangeably herein refers to a monovalent or multivalent monocyclic, bicyclic or tricyclic ring system containing 3 to 14 ring atoms of which one or more ring atoms are selected from heteroatoms, wherein the heteroatom is as defined herein, and which is completely saturated or contains one or more units of unsaturation, but an aromatic ring can not exist in the heterocyclyl group. In one embodiment, a "heterocycle", "heterocyclyl" or "heterocyclic" group is a 3- to 8-membered monocyclic ring (2-6 carbon atoms and 1-3 heteroatoms selected from N, O, P and S, wherein S or P is optionally substituted with one or more oxygen atoms to give a group such as SO, $SO_2$, PO or $PO_2$, when the ring is a 3-membered ring, the ring member contains only one heteroatom), or a 7-12 membered bicyclic ring (4-9 carbon atoms and 1-3 heteroatoms selected from N, O, P and S, where S or P is optionally substituted with one or more oxygen atom to obtain a group such as SO, $SO_2$, PO or $PO_2$). The heterocyclyl group is optionally substituted with one or more substituents described herein.

The heterocyclyl group may be a carbon radical or a heteroatom radical, of which a —$CH_2$— group can optionally be replaced by a —C(=O)— group. Ring sulfur atoms may be optionally oxidized to form S-oxides, and ring nitrogen atoms may be optionally oxidized to form N-oxides. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl, and the like. Some non-limiting examples of heterocyclyl wherein —$CH_2$— group is replaced by —C(=O)— moiety include 2-oxopyrrolidinyl, oxo-1,3-thiazolidinyl, 2-piperidinonyl, 3,5-dioxopiperidinyl, pyrimidindionyl, and the like. Some non-limiting examples of heterocyclyl wherein the ring sulfur atom is oxidized is sulfolanyl and 1,1-dioxo-thiomorpholinyl, etc. The heterocyclyl group is optionally substituted with one or more substituents described herein.

The term "aryl" refers to a monocyclic, bicyclic, or tricyclic carbocyclic ring system having a total of 6 to 14 ring members, or 6 to 10 ring members, or 6 ring members, and wherein at least one ring in the system is aromatic. The aryl group is generally, but not necessarily bonded to the parent molecule through an aromatic ring of the aryl group. The term "aryl" may be used interchangeably with the term "aryl ring" or "aromatic ring". Examples of aryl group may include phenyl, naphthyl and anthracene, etc. The aryl group is optionally substituted with one or more substituents disclosed herein.

The term "heteroaryl" refers to a monocyclic, bicyclic, or tricyclic ring system having a total of 5 to 14 ring members, or 5 to 10 ring members, or 5 to 6 ring members, and wherein at least one ring in the system is aromatic and at least one ring in the system contains one or more heteroatoms. The heteroaryl group is generally, but not necessarily bonded to the parent molecule through an aromatic ring of the aryl group. The term "heteroaryl" may be used interchangeably with the term "heteroaryl ring", "aromatic heterocyclic" or the term "heteroaromatic compound". The heteroaryl group is optionally substituted with one or more substituents disclosed herein. In one embodiment, the heteroaryl group is a 5- to 10-membered heteroaryl comprising 1, 2, 3 or 4 heteroatoms independently selected from 0, S and N; in another embodiment, the heteroaryl group is a 5- to 6-membered heteroaryl comprising 1, 2, 3 or 4 heteroatoms independently selected from O, S and N.

Some non-limiting examples of heteroaryl group include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, etc, and the following bicycles, but are not limited to: benzimidazolyl, benzofuryl, benzothienyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl, and the like.

The term "stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

The term "tautomer" or "tautomeric form" refers to structural isomers of different energies which are interconvertible via a low energy barrier. Where tautomerization is possible (e.g., in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

A "solvate" refers to an association or complex of one or more solvent molecules and a compound disclosed herein. Some non-limiting examples of solvents that form solvates include water, isopropanol, ethanol, methanol, dimethylsulfoxide, ethyl acetate, acetic acid, ethanolamine, or mixture thereof. The term "hydrate" refers to the complex where the solvent molecule is water.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in *J. Pharmacol Sci*, 1977, 66, 1-19, which is incorporated herein by reference. Some non-limiting examples of pharmaceutically acceptable and nontoxic salts formed with acid include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oilsoluble or dispersable products may be obtained by such quaternization. Alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

BRIEF DESCRIPTION OF THE DRAWINGS

FIG. 1 is an average drug-time curve of a compound according to example B in rats of the present invention.

DESCRIPTION OF THE PREFERRED EMBODIMENTS

Embodiments of the present invention is described in detail below, and exemplary embodiments of the embodiment are shown in the accompanying drawings, wherein same or similar reference numerals throughout the separate views refer to the same or similar elements or functionally similar or identical elements. The embodiments described below with reference to the drawings are intended to be illustrative of the invention and are not to be construed as limiting the present invention.

In the examples described below, unless otherwise indicated all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjin Fuchen Chemical Reagent Factory, Wuhan XinHuayuan Technology Development Co., Ltd., Qingdao Tenglong Reagent Chemical Ltd., and Qingdao Ocean Chemical Factory.

Anhydrous THF, 1,4-dioxane, toluene, and ethyl ether were obtained by refluxing the solvent with sodium. Anhydrous dichloromethane and anhydrous chloroform were obtained by drying dichloromethane and chloroform independently in the refluxing condition equipped with hydride calcium. Ethyl acetate, petroleum ether, n-hexane, N,N-dimethylacetamide and N,N-dimethylformamide were dried over anhydrous sodium sulfate before use.

Column chromatography was conducted using a silica gel column. Silica gel (300-400 mesh) was purchased from Qingdao Ocean Chemical Factory.

$^1$H NMR spectra were recorded on a Bruker 400 MHz or 600 MHz NMR spectrometer. $^1$H NMR spectra were obtained by using $CDCl_3$, $DMSO-d_6$, $CD_3OD$ or $acetone-d_6$ as solvent (reported in ppm), and TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants, when given, were reported in Hertz (Hz).

Low resolution mass spectrometry (MS) data was determined on an Agilent 6120 quadrupole HPLC-M (column model: Zorbax SB-C18, 2.1×30 mm, 3.5 microns, 6 min, flow rate 0.6 ml/min). Mobile phase: 5%-95% (0.1% formic acid in $CH_3CN$) in (0.1% formic acid in water), electrospray ionization (ESI) was used. HPLC chromatogram was recorded using a UV-Vis wavelength detector at 210/254 nm.

Purities of compounds were assessed by Agilent 1260 Series pre-HPLC or Calesep pump 250 pre-HPLC (column model: NOVASEP 50/80 mm DAC) with UV detection at 210 nm and 254 nm.

The following abbreviations are used throughout the specification:
WTXT Vortioxetine
mL milliliter
min minute, minutes
g gram
mg milligram
ng nanogram
h hour, hours
DMF N,N-dimethylformamide
Et$_3$N triethylamine
EA, EtOAc ethyl acetate
CDCl$_3$ Deuterated chloroform
DMSO dimethylsulfoxide
Cs$_2$CO$_3$ cesium carbonate
DMDO-OH 4-(hydroxymethyl)-5-methyl-[1,3]dioxole-2-one
DCM dichloromethane
1N 1 mol/L
mL, ml milliliter
mmol, mM millimole
Tween-20 Tween-20
Span-20 Span-20

EXAMPLES

Example 1
1-(2-((2,4-dimethylphenyl)thio)phenyl)piperazine Stearate

Synthetic Operation:

To a 100 ml single-neck flask were added WTXT00 (4.0 g), acetone (80 mL) and stearic acid (4.4 g). The mixture was heated to 50° C. and stirred for 30 min. The mixture was clear, and cooled to 0° C., and a solid precipitated out. The mixture was filtered, and the filter cake was dried in vacuo at 45° C. to give compound (1) (6.4 g), purity: 99.95%.

$^1$H NMR (600 MHz, CDCl$_3$): δ11.0 (br s, 1H), 6.96-7.02 (m, 2H), 6.82 (m, 1H), 6.67 (m, 2H), 6.40 (m, 2H), 3.47 (t, 4H), 2.78 (t, 4H), 2.35 (s, 6H) 2.23 (m, 2H), 2.0 (br s, 1H), 1.56 (m, 2H), 1.30-1.33 (m, 28H), 0.96 (t, 3H).

Example 2
1-(2-((2,4-dimethylphenyl)thio)phenyl)piperazine Palmitate

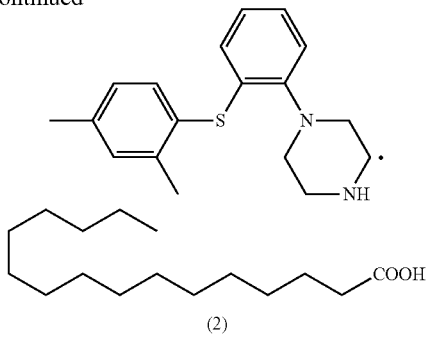

(2)

Synthetic Operation:

To a 100 ml single-neck flask were added WTXT00 (4.0 g), acetone (80 mL) and palmitic acid (3.8 g). The mixture was heated to 50° C. and stirred for 30 min. The mixture was clear, and cooled to 0° C., and a solid precipitated out. The mixture was filtered, and the filter cake was dried in vacuo to give compound (2) (5.4 g), purity: 99.98%.

$^1$HNMR (600 MHz, CDCl$_3$): δ11.0 (br s, 1H), 6.96-7.02 (m, 2H), 6.82 (m, 1H), 6.67 (m, 2H), 6.40 (m, 2H), 3.47 (t, 4H), 2.78 (t, 4H), 2.35 (s, 6H) 2.23 (m, 2H), 2.0 (br s, 1H), 1.56 (m, 2H), 1.30-1.33 (m, 24H), 0.96 (t, 3H).

Example 3 acetoxymethyl 1-(2-((2,4-dimethylphenyl)thio)phenyl)piperazinylcarboxylate

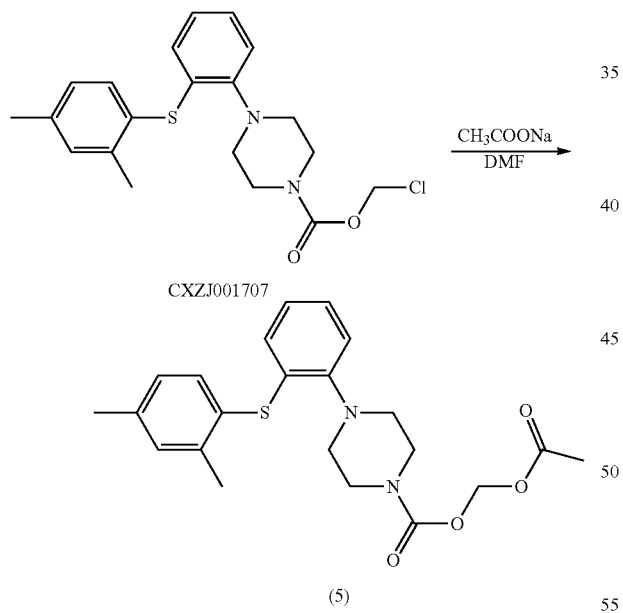

CXZJ001707

(5)

Synthetic Operation:

To a 50 ml reaction flask were added CXZJ001707 (2.0 g), sodium acetate (1.26 g) and DMF (20 ml). The mixture was stirred at 90° C. for 15 hours and the reaction was monitored by TLC. When the reaction was completed, the mixture was extracted with toluene, washed with water and concentrated. The residue was crystalized in n-heptane (30 ml) at 0° C., and the mixture was filtered. The filter cake was dried in vacuo at 50° C. for 10 h to give the objective compound (5) (1.2 g), and the purity by HPLC was 97.92%. LC-MS: M+H: 415;

$^1$H NMR (600 MHz, CDCl$_3$): δ 7.02 (m, 2H), 6.87 (s, 2H), 6.82 (m, 1H), 6.67 (m, 2H), 6.40 (m, 2H), 3.61 (m, 4H), 3.19 (m, 4H), 2.35 (s, 6H), 2.01 (s, 3H).

Example 4
1-(2-((2,4-dimethylphenyl)thio)phenyl)piperazine Laurate (3)

Synthetic Operation:

To a 500 ml reaction flask were added WTXT (20 g), DCM (200 mL) and sodium hydroxide solution (20 mL, 25%). The mixture was stirred for 30 min to clear, and stood for partition. The organic layers were washed with water (200 mL), and the aqueous layer was abandoned. The organic layer was concentrated to give oil, and to the oil was added methyl tert-butyl ether (50 mL). The mixture was stirred at room temperature for 2 h, then filtered. The solid was dried at 40° C. in vacuo to give free base WTXT00 (12 g).

To a 100 ml single-neck flask were added WTXT00 (4.0 g), acetone (80 mL) and lauric acid (3 g). The mixture was heated to 50° C. and stirred for 30 min. The mixture was clear, and cooled to 0° C., and a solid precipitated out. The mixture was filtered, and the filter cake was concentrated in vacuo at 45° C. to give compound (3) (3.2 g), purity: 99.93%.

$^1$H NMR (600 MHz, CDCl$_3$): δ11.0 (br s, 1H), 6.96-7.02 (m, 2H), 6.82 (m, 1H), 6.67 (m, 2H), 6.40 (m, 2H), 3.47 (t, 4H), 2.78 (t, 4H), 2.35 (s, 6H) 2.23 (m, 2H), 2.0 (br s, 1H), 1.56 (m, 2H), 1.30-1.33 (m, 16H), 0.96 (t, 3H).

Example 5 ethyl 1-(2-((2,4-dimethylphenyl)thio) phenyl)piperazinylcarboxylate

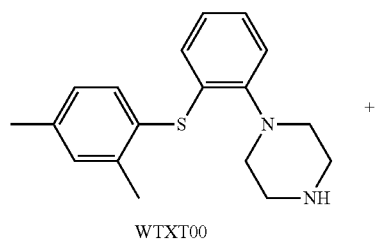
WTXT00

+

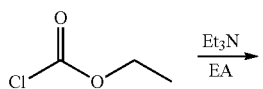
$\xrightarrow{\text{Et}_3\text{N}}{\text{EA}}$

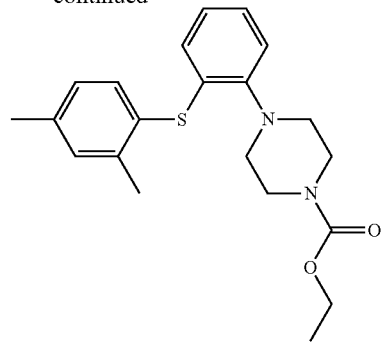

(6)

Synthetic Operation:

To a 250 ml reaction flask were added WTXT00 (5 g), EA (100 ml) and Et$_3$N (2.02 g). The mixture was stirred at 0° C., and a solution of ethyl chloroformate (2.16 g) in EA (50 ml) was added dropwise. After dropwise addition, the mixture was reacted and detected by TLC. After the reaction was completed, the mixture was washed with water for two times, and anhydrous sodium sulfate was added. Then the mixture was stood for 2 h, and filtered. The organic layer was concentrated, and to the residue was added n-heptane (30 ml). The resulting mixture was stirred overnight, filtered, and the solid was dried in vacuo at 45° C. for 8 h to give compound (6) (3.02 g), purity: 99.41%.

LC-MS: M+H: 371;

$^1$H NMR (600 MHz, DMSO): δ 7.35 (d, 1H), 7.24 (s, 1H), 7.12 (m, 3H), 6.92 (m, 1H), 6.40 (m, 1H), 4.12 (q, J=8.0 Hz, 2H), 3.61 (m, 4H), 3.19 (m, 2H), 2.35 (s, 6H), 1.21 (t, J=8.0 Hz, 3H).

Example 6 (dodecanoyloxy)methyl 1-(2-((2,4-dimethylphenyl)thio)phenyl) Piperazinylcarboxylate

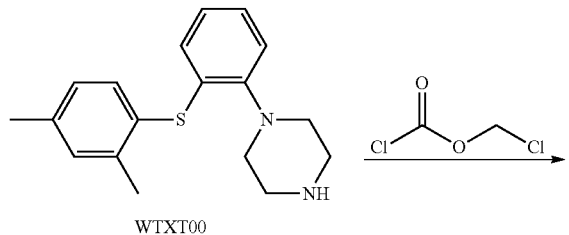
WTXT00

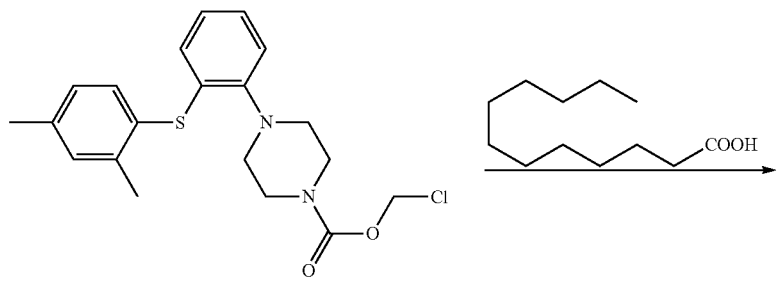
CXZJ001707

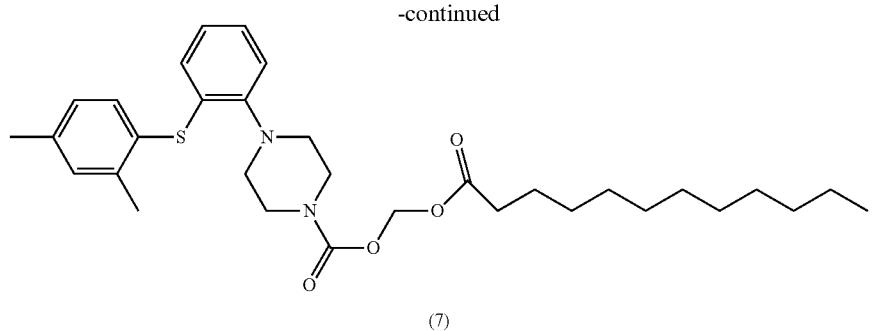

(7)

Synthetic Operation:

To a 1000 ml single-neck flask were added WTXT00 (20 g), triethylamine (1.8 g) and EA (400 mL). The mixture was cooled to 0° C., and a solution of chloromethyl chloroformate (10.36 g) in EA (200 mL) was added into the mixture. The resulting mixture was stirred for 2 h, and the reaction was detected by TLC until the raw material was disappeared. The reaction mixture was washed with water (200 mL), and the organic layer was concentrated. To the residue was added n-heptane (100 mL), and the mixture was stirred for 2 h, then filtered. The solid was dried in vacuo at 45° C. for 10 h to give intermediate product CXZJ001707 (24.4 g), and the purity detected by HPLC was 95.30%.

To a 50 ml reaction flask were added CXZJ001707 (3.0 g), sodium bicarbonate (2.0 g), sodium iodide (0.57 g), DMF (20 ml), lauric acid (3.0 g). The mixture was heated to 100° C. for 3 h. The reaction monitored was almost completed, then the mixture was cooled to room temperature, and water (30 mL) was added. A stick solid precipitated out, and the mixture was extracted with toluene (30 mL). The organic layer was concentrated to give compound (7) (3.0 g), and the purity detected by HPLC was 97.89%.

LC-MS: M+H: 555;

$^1$H NMR (600 MHz, CDCl$_3$): δ 7.38 (m, 1H), 7.17 (m, 1H), 6.98-7.11 (m, 3H), 6.91 (m, 1H), 6.56 (m, 1H), 5.84 (s, 2H), 3.81 (m, 4H), 3.06 (m, 4H), 2.27-2.42 (m, 8H), 1.67 (m, 2H), 1.28 (m, 16H), 0.93 (m, 3H).

Example 7 (heptadecanoyloxy)methyl 1-(2-((2,4-dimethylphenyl)thio)phenyl) Piperazinylcarboxylate

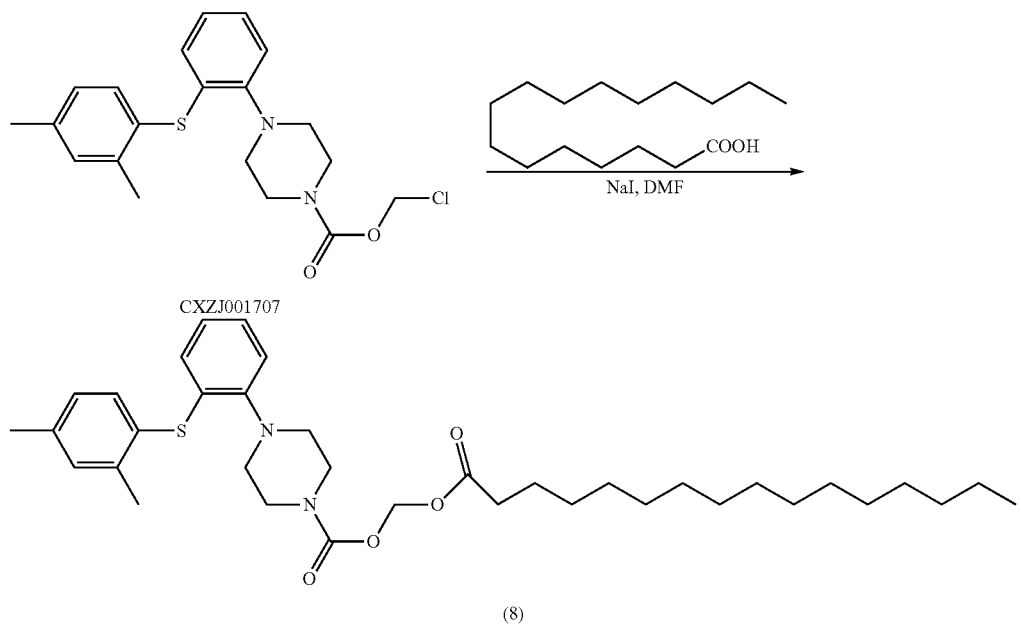

(8)

Synthetic Operation:

To a 50 ml reaction flask were added CXZJ001707 (2.0 g), palmitic acid (2.62 g), cesium carbonate (1.67 g) and DMF (26 ml). The mixture was stirred at 60° C. for 17 hours, then a sample of mixture was took and detected, and the reaction was completed. The mixture was extracted with toluene, the organic layer was washed with water and concentrated. The residue was triturated with n-heptane (20 ml), and the mixture was filtered. The filter cake was dried in oven to give compound (8) (2.1 g).

LC-MS: M+H: 611;

$^1$H NMR (600 MHz, CDCl$_3$): δ 7.38 (m, 1H), 7.17 (m, 1H), 6.98-7.11 (m, 3H), 6.91 (m, 1H), 6.56 (m, 1H), 5.84 (s, 2H), 3.81 (m, 4H), 3.06 (m, 4H), 2.27-2.42 (m, 8H), 1.67 (m, 2H), 1.28 (m, 24H), 0.93 (m, 3H)

Example 8 (stearoyloxy)methyl 1-(2-((2,4-dimethylphenyl)thio)phenyl)piperazinyl Carboxylate

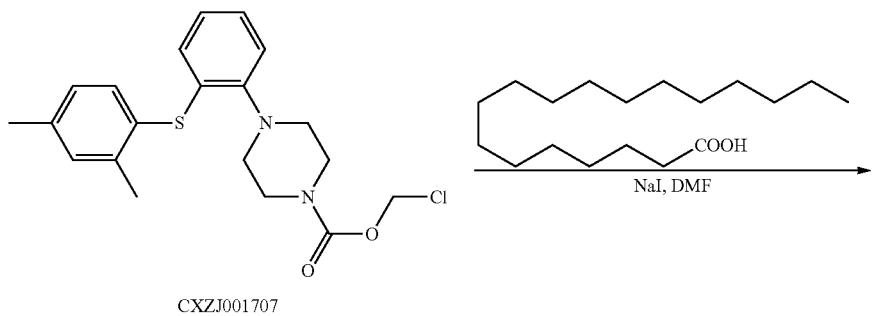

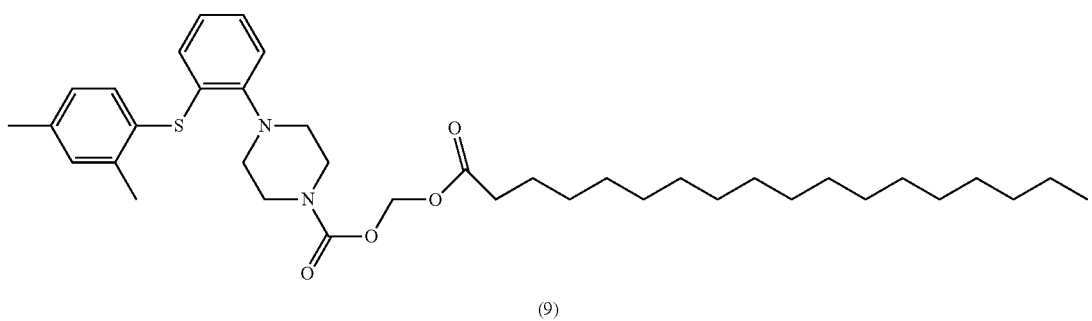

Synthetic Operation:

To a 100 ml reaction flask were added CXZJ001707 (3.0 g), stearic acid (4.37 g), cesium carbonate (2.50 g) and DMF (40 ml). The mixture was stirred at 60° C. for 15 hours, then the reaction detected by TLC was completed. The mixture was extracted with toluene, the organic layer was washed with water and concentrated. The residue was triturated with n-heptane (30 ml), and the mixture was filtered. The filter cake was dried in oven to give the objective compound (9) (3.5 g).

LC-MS: M+H: 639;

$^1$H NMR (600 MHz, CDCl$_3$): δ 7.38 (m, 1H), 7.17 (m, 1H), 6.98-7.11 (m, 3H), 6.91 (m, 1H), 6.56 (m, 1H), 5.84 (s, 2H), 3.81 (m, 4H), 3.06 (m, 4H), 2.27-2.42 (m, 8H), 1.67 (m, 2H), 1.28 (m, 28H), 0.93 (m, 3H).

Example 9 (benzoyloxy)methyl 1-(2-((2,4-dimethylphenyl)thio)phenyl)piperazinyl Carboxylate

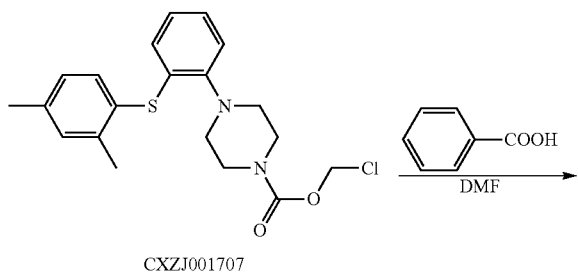

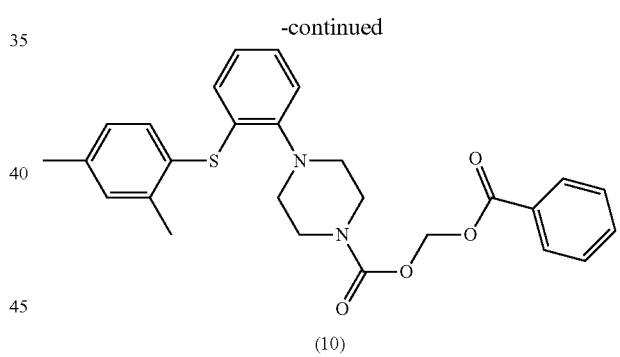

Synthetic Operation:

To a 100 ml reaction flask were added CXZJ001707 (3.9 g), benzoic acid (3.36 g), Cs$_2$CO$_3$ (2.0 g), and DMF (40 ml). The mixture was stirred at 90° C. for 4 hours and the reaction monitored by TLC was completed. The mixture was washed with water (40 ml), and extracted with toluene (40 ml). The organic layer was concentrated. The residue was triturated with n-heptane (30 ml) for crystallization. The mixture was filtered. The filter cake was dried in vacuo at 50° C. for 10 h to give the object compound (10) (4.4 g), and the purity detected by HPLC was 97.6%.

LC-MS: M+H: 477;

$^1$H NMR (600 MHz, CDCl$_3$): δ 8.14 (d, J=12 Hz, 2H), 7.62 (t, J=6 Hz, 1H), 7.49 (t, J=6 Hz, 2H), 7.35 (d, J=12 Hz, 1H), 7.17 (s, 1H), 7.06 (m, 3H), 6.92 (m, 1H), 6.56 (d, J=6 Hz, 1H), 6.10 (s, 2H), 3.06 (m, 4H), 3.73 (s, 4H), 3.06 (d, J=36 Hz, 4H), 2.38 (s, 3H), 2.34 (s, 3H).

Example 10 (5-methyl-2-oxo-1,3-dioxol-4-yl) methyl 1-(2-((2,4-dimethylphenyl)thio) phenyl)piperazinylcarboxylate

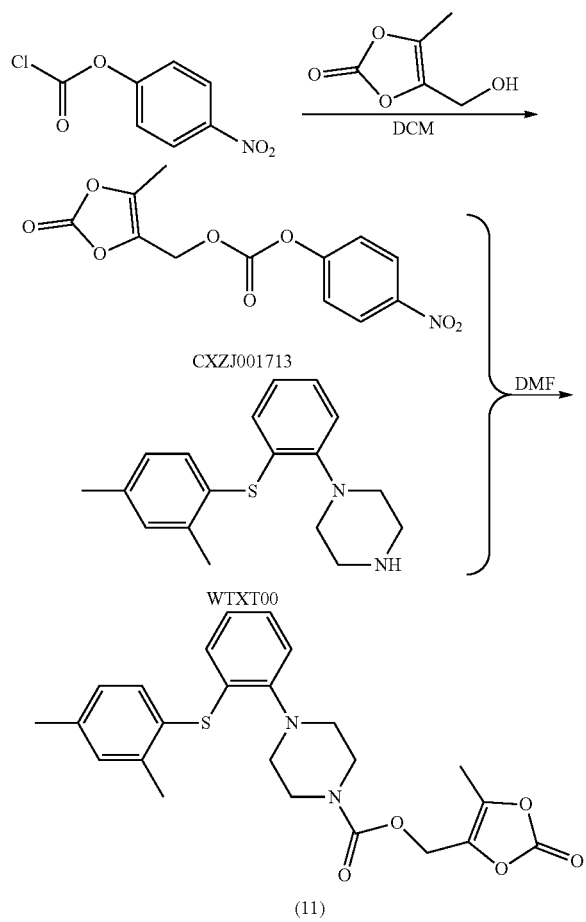

(11)

Synthetic Operation:

To a 100 mL reaction flask were added DMDO-OH (3.0 g), pyridine (1.9 g) and DCM (25 mL). The solution was cooled to 0° C., and a solution of nitrophenyl carbonochloridate (4.9 g) in DCM (25 ml) was added dropwise into the solution. After addition, the mixture was reacted at rt overnight, and the reaction was completed by detecting a sample of the mixture. The reaction mixture was washed with 1% aqueous sodium hydroxide solution and hydrochloric acid (1 N), and the organic layer was concentrated. The residue was triturated with toluene (50 mL) at room temperature, and the mixture was filtered. The filter cake was dried at 45° C. in vacuo to give intermediate CXZJ001713 (3 g, HPLC purity: 97.6%).

To a 250 mL reaction flask were added WTXT00 (2.8 g), CXZJ001713 (3.0 g) and DMF (60 ml). The mixture was stirred at 20° C. for 3 to 4 h. After the reaction was basically finished by taking and detecting a sample, to the mixture was added dropwise water (50 mL), and a solid precipitated out. The mixture was filtered, and the solid was added into isopropyl ether (60 mL), then the mixture was stirred at 20° C. overnight. The resulting mixture was filtered, and the solid was dried in vacuo at 45° C. for 12 h to give a white solid compound (11) (3.4 g), the purity detected by HPLC was 97.7%.

LC-MS: M+H: 455;

$^1$H NMR (600 MHz, CDCl$_3$): δ 7.38 (m, 1H), 7.18 (s, 1H), 7.03-7.12 (m, 3H), 6.91 (m, 1H), 6.56 (m, 1H), 4.91 (s, 2H), 3.69 (m, 4H), 3.06 (m, 4H), 2.38 (s, 3H), 2.34 (s, 3H), 2.23 (s, 3H).

Example 11 (butyryloxy)methyl 1-(2-((2,4-dimethylphenyl)thio)phenyl)piperazinyl Carboxylate

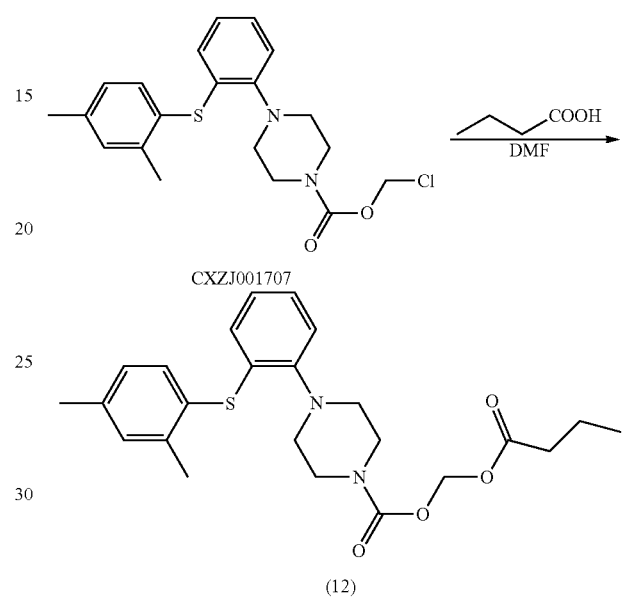

(12)

Synthetic Operation:

To a 100 ml reaction flask were added CXZJ001707 (3.0 g), n-butyric acid (1.35 g), Cs$_2$CO$_3$ (2.5 g), and DMF (40 ml). The mixture was stirred at 60° C. for 12 hours and the reaction monitored by TLC was completed. The mixture was washed with water (40 ml), and extracted with toluene (40 ml). The organic layer was concentrated to give the objective compound (12) (3.0 g), and the purity detected by HPLC was 95.9%.

LC-MS: M+H: 443;

$^1$H NMR (600 MHz, CDCl$_3$): δ 7.02 (m, 2H), 6.87 (s, 2H), 6.82 (m, 1H), 6.67 (m, 2H), 6.40 (m, 2H), 3.61 (m, 4H), 3.19 (m, 4H), 2.35 (s, 6H), 2.25 (m, 2H), 1.72 (m, 2H), 0.96 (m, 3H).

Example 12 (hexanoyloxy)methyl 1-(2-((2,4-dimethylphenyl)thio)phenyl)piperazinyl Carboxylate

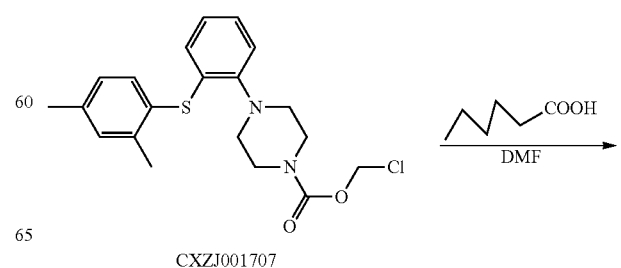

CXZJ001707

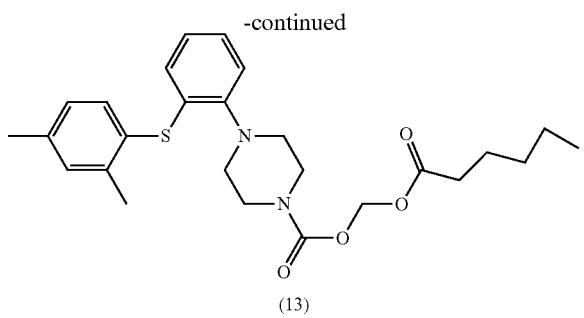

(13)

Synthetic Operation:

To a 100 ml reaction flask were added CXZJ001707 (2.0 g), n-hexylic acid (1.2 g), Cs$_2$CO$_3$ (1.66 g), and DMF (27 ml). The mixture was stirred at 60° C. for 12 hours and the reaction monitored by TLC was completed. The mixture was washed with water (40 ml), and extracted with toluene (40 ml). The organic layer was concentrated to give the objective compound (13) (2.1 g), and the purity detected by HPLC was 95.1%.

LC-MS: M+H: 471;
$^1$H NMR (600 MHz, CDCl$_3$) δ 7.28 (s, 1H), 7.20 (s, 1H), 6.89 (s, 2H), 6.62 (s, 1H), 6.55 (d, J=20.0 Hz, 2H), 6.36 (s, 2H), 3.30 (d, J=15.0 Hz, 8H), 2.40-2.24 (m, 8H), 1.66 (s, 2H), 1.29 (d, J=40.0 Hz, 4H), 0.89 (s, 3H).

Example 13 (octanoyloxy)methyl 1-(2-((2,4-dimethylphenyl)thio)phenyl)piperazinyl Carboxylate

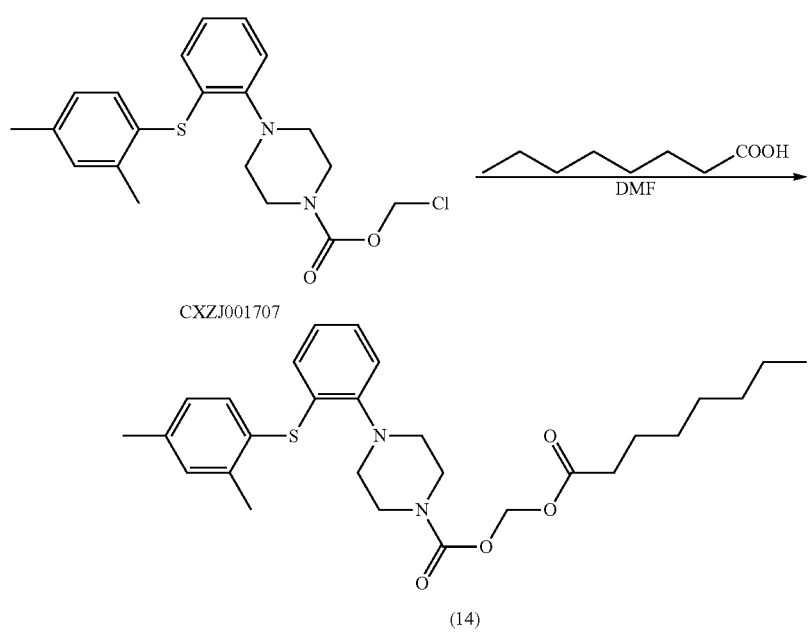

(14)

Synthetic Operation:

To a 100 ml reaction flask were added CXZJ001707 (2.0 g), octanoic acid (1.5 g), Cs$_2$CO$_3$ (1.66 g), and DMF (27 ml). The mixture was stirred at 60° C. for 12 hours and the reaction monitored by TLC was completed. The mixture was washed with water (40 ml), and extracted with toluene (40 ml). The organic layer was concentrated to give the objective compound (14) (2.0 g), and the purity detected by HPLC was 94.5%.

LC-MS: M+H: 499;
$^1$H NMR (600 MHz, CDCl$_3$) δ 7.26 (s, 1H), 7.18 (s, 1H), 6.87 (s, 2H), 6.64-6.47 (m, 3H), 6.33 (s, 2H), 3.30 (d, J=15.0 Hz, 8H), 2.40-2.22 (m, 8H), 1.66 (s, 2H), 1.29 (d, J=34.9 Hz, 8H), 0.89 (s, 3H).

Example 14 (decanoyloxy)methyl 1-(2-((2,4-dimethylphenyl)thio)phenyl)piperazinyl Carboxylate

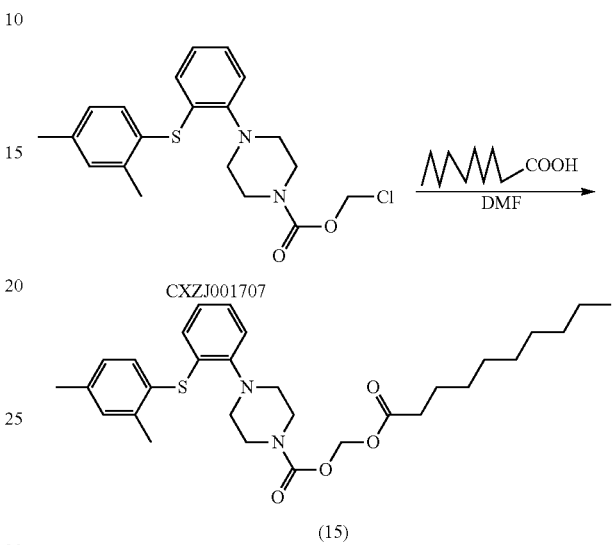

(15)

Synthetic Operation:

To a 100 ml reaction flask were added CXZJ001707 (2.0 g), decanoic acid (1.76 g), Cs$_2$CO$_3$ (1.66 g) and DMF (27 ml). The mixture was stirred at 60° C. for 12 hours and the reaction monitored by TLC was completed. The mixture was washed with water (40 ml), and extracted with toluene (40 ml). The organic layer was concentrated to give the objective compound (15) (2.2 g), and the purity detected by HPLC was 94.9%.

LC-MS: M+H: 527;

¹H NMR (600 MHz, CDCl₃) δ7.27 (s, 1H), 7.19 (s, 1H), 6.88 (s, 2H), 6.64-6.48 (m, 3H), 6.34 (s, 2H), 3.30 (d, J=15.0 Hz, 8H), 2.41-2.22 (m, 8H), 1.66 (s, 2H), 1.29 (d, J=35.0 Hz, 12H), 0.89 (s, 3H).

Example 15 (tetradecanoyloxy)methyl 1-(2-((2,4-dimethylphenyl)thio)phenyl) Piperazinylcarboxylate

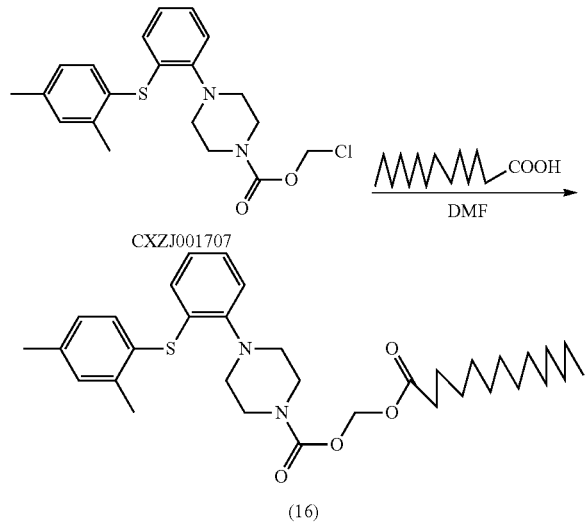

Synthetic Operation:

To a 100 ml reaction flask were added CXZJ001707 (2.0 g), tetradecanoic acid (2.3 g), Cs₂CO₃ (1.66 g) and DMF (27 ml). The mixture was stirred at 60° C. for 12 hours and the reaction monitored by TLC was completed. The mixture was washed with water (40 ml), and extracted with toluene (40 ml). The organic layer was concentrated to give the objective compound (16) (2.5 g), and the purity detected by HPLC was 94.2%.

LC-MS: M+H: 584;

¹H NMR (600 MHz, CDCl₃) δ 7.28 (s, 1H), 7.20 (s, 1H), 6.89 (s, 2H), 6.65-6.48 (m, 3H), 6.34 (s, 2H), 3.30 (d, J=15.0 Hz, 8H), 2.42-2.18 (m, 8H), 1.66 (s, 2H), 1.35-1.22 (m, 20H), 0.89 (s, 3H).

Example 16
1-(2-((2,4-dimethylphenyl)thio)phenyl)piperazine Pamoate

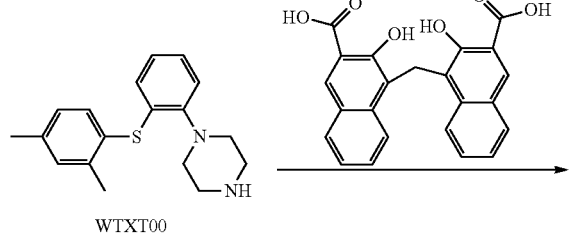

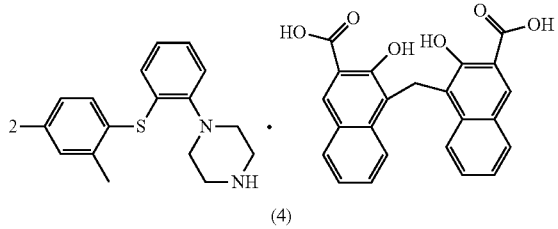

Synthetic Operation:

To a 100 ml single-neck flask were added WTXT00 (2.0 g), acetone (80 mL) and pamoic acid (5.7 g). The mixture was heated to 60° C. and stirred for 30 min. The mixture was clear, and cooled to 0° C., and a solid precipitated out. The mixture was filtered, and the filter cake was concentrated in vacuo at 45° C. to give compound (4) (6.2 g), purity: 99.4%.

¹H NMR (600 MHz, CDCl₃): δ 8.43 (s, 2H), 8.13 (s, 2H), 7.80 (s, 2H), 7.41-7.13 (m, 8H), 6.89 (s, 4H), 6.67-6.46 (m, 6H), 4.82 (s, 2H), 3.46 (s, 8H), 2.81 (s, 8H), 2.32 (d, J=15.0 Hz, 12H), 1.88 (s, 2H).

Biological Test Data

The LC/MS/MS system for analysis consists of the Agilent 1200 series vacuum degassing furnace, binary syringe pump, well plate autosampler, column incubator, and Agilent G6430 three-stage quadrupole mass spectrometer equipped with electro spray ionization (ESI) source. Quantitative analysis was performed in MRM mode, and the parameters of MRM conversion were shown in Table A.

TABLE A

| | |
|---|---|
| Multiple reaction monitoring scan | 299.1→150 |
| Fragmentor voltage | 25 V |
| Capillary voltage | 3500 V |
| Temperature of dryer | 350° C. |
| Nebulizer | 40 psi |
| The flow rate of dryer | 9 mL/min |

Agilent Poroshell HPH-C18, 2.1×50 mm, 2.7 μM column was used for analysis, and 20 μL of sample was injected. Analytical conditions: the mobile phase was (2 mM ammonium formate+0.1% formic acid) (A) and (methanol+2 mM ammonium formate+0.1% formic acid) (B). The flow rate was 0.3 mL/min. The mobile phase gradient was shown in Table B.

TABLE B

| Hours | Gradient of mobile phase B (WTXT\Example 1\Example 2) |
|---|---|
| 1.1 min | 5% |
| 1.2 min | 75% |
| 1.8 min | 85% |
| 2.6 min | 85% |
| 2.7 min | 5% |
| 4.0 min | stop or |

| Time | Gradient of mobile phase B (WTXT\Example 1\Example 3) |
|---|---|
| 0.5 min | 10% |
| 0.8 min | 85% |
| 2.7 min | 90% |
| 2.8 min | 10% |
| 4.0 min | stop or |

TABLE B-continued

| Time | Gradient of mobile phase B (Example 9\Example 11) |
|---|---|
| 0.5 min | 10% |
| 1.5 min | 85% |
| 2.7 min | 85% |
| 2.71 min | 10% |
| 4.0 min | stop or |

| Time | Gradient of mobile phase B (Example 9\Example 11) |
|---|---|
| 0.5 min | 20% |
| 1.0 min | 100% |
| 2.7 min | 100% |
| 2.8 min | 20% |
| 4.0 min | stop |

In addition, the Agilent 6330 Series LC/MS/MS spectrometer for analysis was equipped with a G1312A binary syringe pump, G1367A autosampler and MS/MS detector; ESI source was used in LC/MS/MS. Each analyte was treated in a suitable cation model and optimally analyzed by MRM conversion with using standard solutions. Agilent Poroshell HPH-C18 columns were used during the analysis, and the size was: 100×4.6 mm I.D., 5 μM. The mobile phase was (2 mM ammonium formate+0.1% formic acid) (A) and (methanol+2 mM ammonium formate+0.1% formic acid) (B). The flow rate was 0.3 mL/min; the column temperature was maintained at 40° C.; 20 μL of sample was injected.

Example A Stability in Human Liver Microsomes

Human liver microsome incubation system was used. Typical incubation mixture consists of human or rat liver microsomes (0.5 mg protein/mL) and target compound (1 μM). The compound was dissolved in DMSO, and diluted with acetonitrile and water, and then mixed with a mixture of liver microsome and potassium phosphate buffer (pH=7.4). All of the above operations were done on wet ice. And the sample solution was incubated in a 37° C. constant incubator. At different time points (0 and 60 min), the reaction was stopped by the addition of ice-cold acetonitrile. The effect of esterase on its transformation was mainly investigated. Samples were stored at −80° C. until LC/MS/MS analysis.

The amount of the compound of the present invention converted into an active arylthiophenylpiperazine compound in the human liver microsome incubation mixture was determined by LC/MS/MS method.

Table 1 lists the data of stability test of some examples in human liver microsomes. As shown in Table 1, the compound of the present invention can be converted into an active arylthiophenylpiperazine compound after being incubated in human liver microsomes.

TABLE 1

Stability data of compounds in human liver microsomes (remaining amount or generating amount of vortioxetine)

| | Compound | | | | | |
|---|---|---|---|---|---|---|
| Time (min) | WTXT | Example 1 Compound (1) | Example 2 Compound (2) | Example 3 Compound (5) | Example 9 Compound (10) | Example 11 Compound (12) |
| | | | | Residual % | | |
| 0 (4° C.) | 100 | 75 | 96 | 0 | 0 | 0 |
| 0 | 108 | 73 | 185 | 119 | 1 | 20 |
| 60 | 99 | 72 | 96 | 107 | 44 | 68 |
| 60 + NADPH | 76 | 60 | 93 | 92 | 38 | 56 |

Note:
WTXT represents vortioxetine

Example B: Pharmacokinetic Evaluation after Administering a Certain Amount of the Compound of the Invention by Intramuscular Injection to Rats The LC/MS/MS system for analysis consists of the Agilent 1200 series vacuum degassing furnace, binary syringe pump, well plate autosampler, column incubator, and API4000 three-stage quadrupole mass spectrometer equipped with electro spray ionization (ESI) source. Quantitative analysis was performed in MRM mode, and the parameters of MRM conversion were shown in Table A.

TABLE A

| Multiple reaction monitoring scan | 299.1→150 |
|---|---|
| Fragmentor voltage | 30 V |
| Capillary voltage | 5500 V |
| Temperature of dryer | 550° C. |
| Gas1 | 50 psi |
| Gas2 | 50 psi |
| CUR | 20 psi |

Waters XBridge™ C18, 2.1×30 mm, 3.5 μM column was used for analysis, and 20 μL of sample was injected. Analytical conditions: the mobile phase was (2 mM ammonium formate+0.1% formic acid) (A) and (methanol+2 mM ammonium formate+0.1% formic acid) (B). The flow rate was 0.5 mL/min. The gradient of mobile phase was shown in Table B.

TABLE B

| Hours | The gradient of Mobile phase B |
|---|---|
| 0.5 min | 20% |
| 1.2 min | 100% |
| 2.7 min | 100% |
| 2.71 min | 20% |
| 4.0 min | stop or |

| Time | The gradient of Mobile phase B |
|---|---|
| 0.5 min | 10% |
| 1.5 min | 85% |
| 2.7 min | 85% |

TABLE B-continued

| | |
|---|---|
| 2.71 min | 10% |
| 4.0 min | stop |

In addition, the API4000 Series LC/MS/MS spectrometer for analysis was equipped with a G1312A binary syringe pump, G1367A autosampler and MS/MS detector; ESI source was used in LC/MS/MS spectrometer. Each analyte was treated in a suitable cation model and optimally analyzed by MRM conversion with using standard solutions. Waters XBridge™ C18 was used during the analysis and the size was: 2.1×30 mm, 3.5 µM. The mobile phase was (2 mM ammonium formate+0.1% formic acid) (A) and (methanol+2 mM ammonium formate+0.1% formic acid) (B). The flow rate was 0.5 mL/min; the column temperature was maintained at 40° C.; 15 µL of sample was injected.

The present invention evaluates the pharmacokinetic study of a series of compounds of the invention in rats. The compound of the present invention was added into a mixture formed by dissolving and dispersing Tween-20 and/or Span-20 in water after being subjected to a pretreatment such as grinding, sieving, etc., and was uniformly dispersed and fixed to a constant volume; the suspension was grinded by a ball mill, then administered. The animals were given a vortioxetine solution (17.5 mg/kg) and a suspension of vortioxetine compound (75 mg/kg) by intramuscular injection. After administration, whole blood was collected at 0.25, 1, 2, 5, 7, 24, 48, 72, 96, 120, 148, and 196 h, and plasma was separated and frozen for testing. And the plasma was centrifuge at 12,000 for 2 minutes. Plasma samples were collected and stored at −20° C. or −70° C. until LC/MS/MS analysis. Table 2 lists the PK data of the series of compounds of the invention in rats. The compounds of the present invention have good pharmacokinetic properties and exhibit different trends in sustained release compared to solutions, including the ideal peak time (Tmax), half-life ($T_{1/2}$) and exposure ($AUC_{last}$), the absorption and release curves are relatively flat compared to the solution, Tmax is between 6-26 h, the blood concentration of vortioxetine at 196 h can be maintained above 7 ng/mL. The average drug-time curve of some of the compounds of the present invention after intramuscular injection in rats is shown in FIG. 1.

TABLE 2 pharmacokinetic data of compounds in rats

| Sample | Dosage form | Dosage (mg/kg) | Sex of rat | Exposure level $AUC_{last}$ (h*ng/ml) | Peak concentration $C_{max}$ (ng/ml) | Half-life period $T_{1/2}$ (hours) h | Time to peak $T_{max}$ (h) |
|---|---|---|---|---|---|---|---|
| WTXT | solution | 17.5 | Male | 1366 | 530.3 | 2.74 | 0.25 |
| Example 1 | Suspension | 75 | Male | 7936 | 119 | 40.0 | 24 |
| Example 2 | Suspension | 75 | Male | 5386 | 99 | 57.2 | 24 |
| Example 3 | Suspension | 75 | Male | 4181 | 61 | 129 | 26 |
| Example 9 | Suspension | 75 | Male | 2031 | 26.2 | 119.6 | 6.3 |
| Example 11 | Suspension | 75 | Male | 4728 | 53.3 | 88.0 | 12.7 |

Note:
WTXT represents vortioxetine compound

Moreover, the terms "first" and "second" are used for descriptive purposes only and are not to be construed as indicating or implying a relative importance or implicitly indicating the number of technical features indicated. Thus, features defining "first" or "second" may include at least one of the features, either explicitly or implicitly. In the description of the present invention, the meaning of "more" is at least two, such as two, three, etc., unless specifically defined otherwise.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments or examples of the specification or the features of them as long as they are not contradictory to one another.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:
1. A compound of Formula (II), or a stereoisomer, a tautomer, a solvate, or a pharmaceutically acceptable salt thereof,

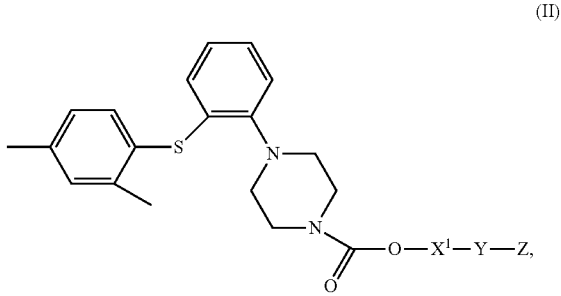

(II)

wherein,
$X^1$ is —$(CH_2)_n$—;
Y is

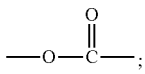

Z is $C_{1-20}$ alkyl, $C_{6-10}$ aryl, $C_{5-10}$ heteroaryl, or $C_{5-10}$ heterocyclyl, wherein optionally each of the $C_{1-20}$ alkyl, $C_{6-10}$ aryl, $C_{5-10}$ heteroaryl and $C_{5-10}$ heterocyclyl is independently substituted with one or more R;
n is 1, 2, 3, 4 or 5; and
each R is independently F, Cl, Br, I, amino, hydroxy or $C_{1-6}$ alkyl.

2. The compound of claim 1, wherein Z is $C_{1-20}$ alkyl, phenyl, $C_{6-8}$ aryl, $C_{5-8}$ heteroaryl, or $C_{5-8}$ heterocyclyl, wherein optionally each of the $C_{1-20}$ alkyl, phenyl, $C_{6-8}$ aryl, $C_{5-8}$ heteroaryl and $C_{5-8}$ heterocyclyl is independently substituted with one or more R;

n is 1, 2 or 3; and each R is independently F, Cl, Br, I, amino, hydroxy or $C_{1-3}$ alkyl.

3. The compound of claim 1 having one of the following structures, or a stereoisomer, a tautomer, a solvate, or a pharmaceutically acceptable salt thereof,

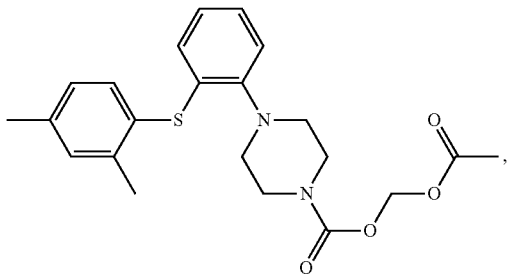

(5)

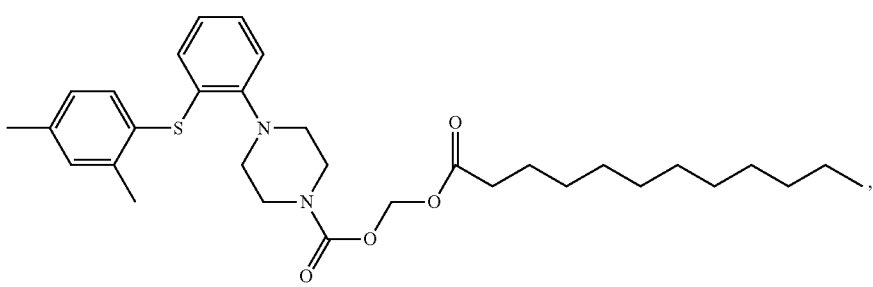

(7)

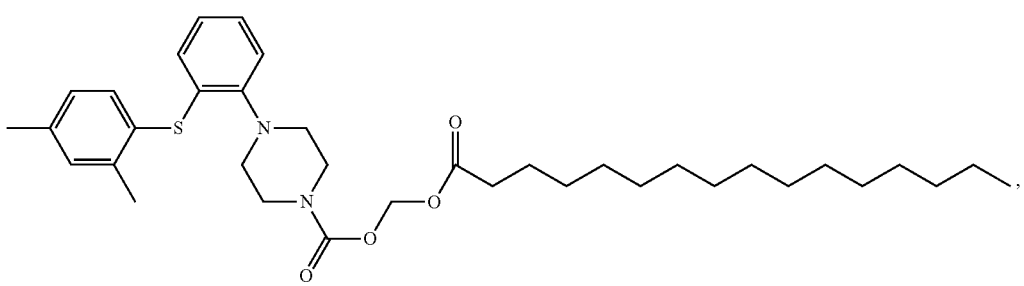

(8)

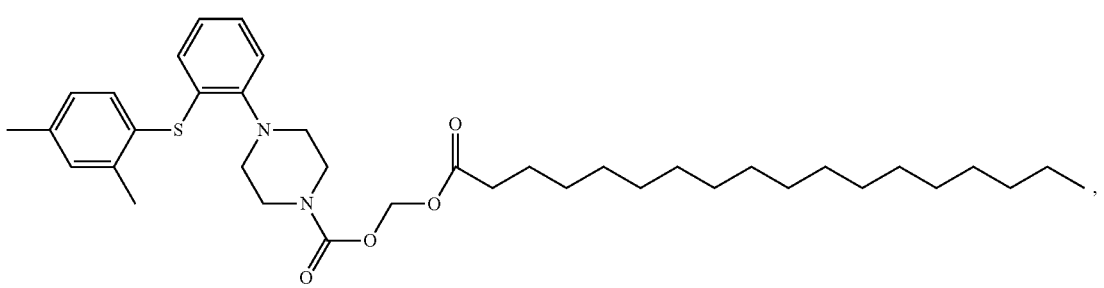

(9)

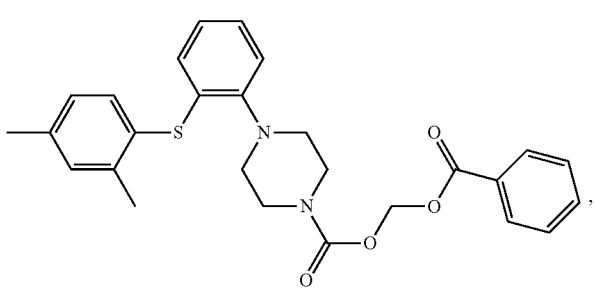

(10)

-continued

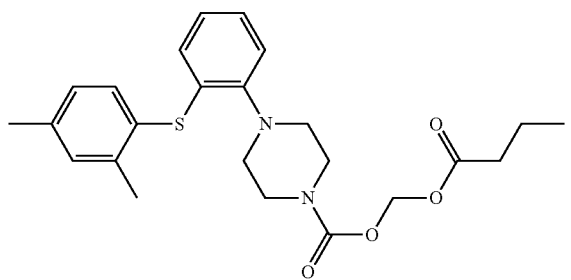
(12)

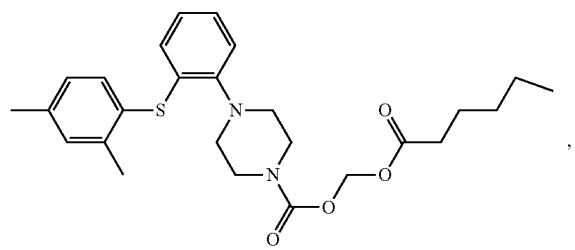
(13)

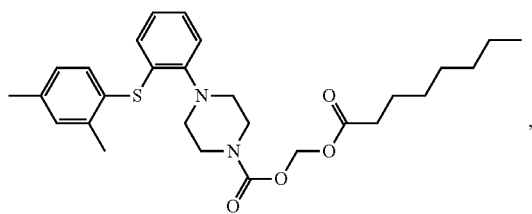
(14)

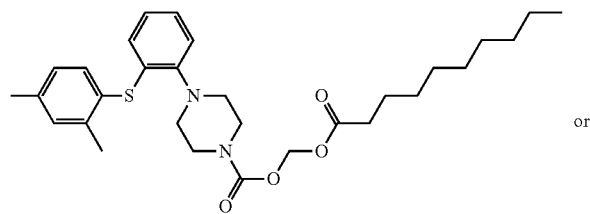
(15)
or

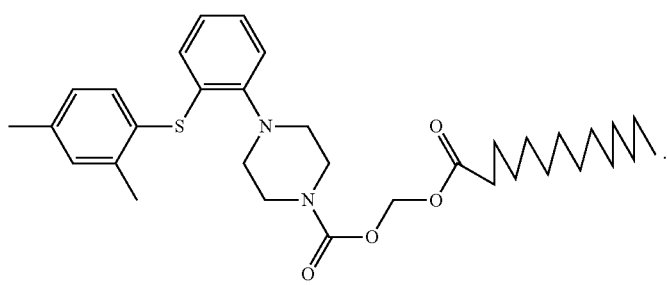
(16)

4. A pharmaceutical composition comprising the compound of claim 1 and a pharmaceutically acceptable carrier, an excipient, a diluent, an adjuvant, a vehicle or a combination thereof.

5. The pharmaceutical composition of claim 4 further comprising an additional therapeutic agent, wherein the additional therapeutic agent is used for treating depressive disorder.

6. A method for preparing the compound of claim 1, comprising:
   (1) contacting a compound of Formula (a) with a compound of Formula (b) to obtain a compound of Formula (c); and
   (2) contacting the compound of Formula (c) with a compound of Formula (d) to obtain a compound of Formula (II), wherein, $X^1$ is $-(CH_2)_n-$;

each $R^1$ is independently F, Cl, Br or I;

Z is $C_{1-20}$ alkyl, $C_{6-10}$ aryl, $C_{5-10}$ heteroaryl, or $C_{5-10}$ heterocyclyl, wherein optionally each of the $C_{1-20}$ alkyl, $C_{6-10}$ aryl, $C_{5-10}$ heteroaryl and $C_{5-10}$ heterocyclyl is independently substituted with one or more R;

n is 1, 2, 3, 4 or 5; and each R is independently F, Cl, Br, I, amino, hydroxy or $C_{1-6}$ alkyl,

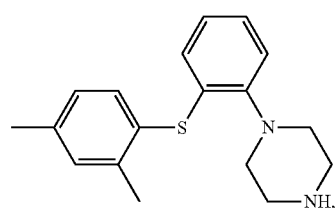
(a)

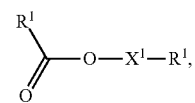
(b)

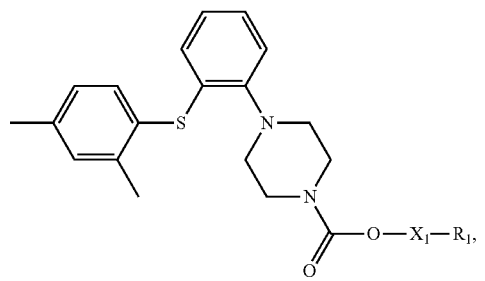
(c)

Z—COOH,
(d)

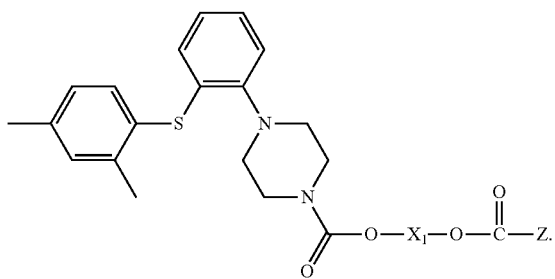
(II)

7. The method of claim 6, wherein Z is $C_{1-20}$ alkyl, phenyl, $C_{6-8}$ aryl, $C_{5-8}$ heteroaryl, or $C_{5-8}$ heterocyclyl, wherein optionally each of the $C_{1-20}$ alkyl, phenyl, $C_{6-8}$ aryl, $C_{5-8}$ heteroaryl and $C_{5-8}$ heterocyclyl is independently substituted with one or more R;

n is 1, 2 or 3; and each R is independently F, Cl, Br, I, amino, hydroxy or $C_{1-3}$ alkyl.

8. A method for treating depressive disorder in a patient comprising administering to the patient the compound of claim 1; and administering to the patient an additional therapeutic agent, wherein the additional therapeutic agent is used for treating depressive disorder.

9. A method for treating depressive disorder in a patient comprising administering to the patient the compound of claim 3; and administering to the patient an additional therapeutic agent, wherein the additional therapeutic agent is used for treating depressive disorder.

10. A method for treating depressive disorder in a patient comprising administering to the patient the pharmaceutical composition of claim 4; and administering to the patient an additional therapeutic agent, wherein the additional therapeutic agent is used for treating depressive disorder.

11. A method for treating depressive disorder in a patient comprising administering to the patient the pharmaceutical composition of claim 5.

* * * * *